United States Patent [19]

Kitson

[11] Patent Number: 5,210,293

[45] Date of Patent: May 11, 1993

[54] PROCESS AND CATALYST FOR THE PRODUCTION OF ETHYLENE AND ACETIC ACID

[75] Inventor: Melanie Kitson, Hull, England

[73] Assignee: BP Chemicals Limited, London, England

[21] Appl. No.: 896,904

[22] Filed: Jun. 11, 1992

Related U.S. Application Data

[63] Continuation of Ser. No. 540,262, Jun. 19, 1990, abandoned.

[30] Foreign Application Priority Data

Jul. 5, 1989 [GB] United Kingdom ................. 8915410

[51] Int. Cl.$^5$ ...................... C07C 27/14; C07C 5/333; C07C 51/215
[52] U.S. Cl. ................................ 562/512.2; 562/548; 562/549; 585/663
[58] Field of Search ..................... 562/548, 549, 512.2; 585/663

[56] References Cited

U.S. PATENT DOCUMENTS

| Re. 31,088 | 11/1982 | Grasselli et al. | 562/535 |
| 2,020,671 | 11/1935 | Dreyfus | 562/549 |
| 3,567,773 | 3/1971 | Yamaguchi et al. | 260/530 |
| 3,751,512 | 8/1973 | Woskow et al. | 260/680 |
| 3,769,239 | 10/1973 | Jogwin | 252/465 |
| 3,840,595 | 10/1974 | Grasselli et al. | 260/530 N |
| 3,856,880 | 12/1974 | Woskow et al. | 260/680 |
| 3,893,951 | 7/1975 | Grasselli et al. | 252/468 |
| 3,956,377 | 5/1976 | Dolhyj et al. | 260/530 N |
| 3,956,378 | 5/1976 | Grasselli et al. | 260/533 N |

(List continued on next page.)

FOREIGN PATENT DOCUMENTS

| 0043684 | 1/1982 | European Pat. Off. . |
| 0167109 | 1/1986 | European Pat. Off. . |
| 0166438 | 6/1986 | European Pat. Off. . |
| 0261264 | 3/1988 | European Pat. Off. . |
| 0294845 | 12/1988 | European Pat. Off. . |
| 1468542 | 2/1970 | Fed. Rep. of Germany . |
| 1542024 | 4/1972 | Fed. Rep. of Germany ...... 268/683 |
| 132335 | 9/1978 | Fed. Rep. of Germany . |
| 2118155B2 | 10/1979 | Fed. Rep. of Germany . |
| WO86/06003 | 10/1986 | PCT Int'l Appl. . |
| 721914 | 1/1955 | United Kingdom . |
| 1309083 | 3/1973 | United Kingdom . |
| 1398385 | 6/1975 | United Kingdom . |
| 1538107 | 1/1979 | United Kingdom . |

OTHER PUBLICATIONS

Abstract of U.S. Pat. No. 4,358,608, Jul. 1991.
Abstract of U.S. Pat. No. 4,250,054, Jul. 1991.
Abstract of U.S. Pat. No. 4,223,161, Jul. 1991.
Abstract of U.S. Pat. No. 4,138,366, Jul. 1991.
Abstract of U.S. Pat. No. 4,115,441, Jul. 1991.
Abstract of U.S. Pat. No. 4,101,448, Jul. 1991.
Abstract of U.S. Pat. No. 4,042,533, Jul. 1991.
Kaneko et al, "Catalytic Oxidation of Olefins . . . " Chemical Abstract, vol. 81, 1974 Abstract #119584f. p. 450.

*Primary Examiner*—José G. Dees
*Assistant Examiner*—Porfirio Nazario
*Attorney, Agent, or Firm*—Nixon & Vanderhye

[57] ABSTRACT

A process and catalyst for the production of ethylene and/or acetic acid by oxidation of ethane and/or ethylene with a molecular oxygen-containing gas in the presence of a catalyst composition comprising the elements A, X and Y in combination with oxygen, the gram-atom ratios of the elements A:X:Y being a:b:c, wherein A=$Mo_dRe_eW_f$; X=Cr, Mn, Nb, Ta, Ti, V and/or W; Y=Bi, Ce, Co, Cu, Fe, K, Mg, Ni, P, Pb, Sb, Si, Sn, Tl and/or U; a=1; b=0 to 2; c=0 to 2; d+e+f=a; d is either zero or greater than zero; e is greater than zero; and f is either zero or greater than zero.

7 Claims, No Drawings

U.S. PATENT DOCUMENTS

| | | | |
|---|---|---|---|
| 4,017,423 | 4/1977 | White et al. | 252/437 |
| 4,041,093 | 8/1977 | Smirnov et al. | 260/673 S |
| 4,042,533 | 8/1977 | Shaw et al. | 252/437 |
| 4,082,698 | 4/1978 | Shaw et al. | 252/469 |
| 4,085,065 | 4/1978 | White et al. | 252/437 |
| 4,139,719 | 2/1979 | White et al. | 562/535 |
| 4,148,757 | 4/1979 | Brazdil et al. | 252/432 |
| 4,157,987 | 6/1979 | Dolhyj et al. | 252/437 |
| 4,163,862 | 8/1979 | Dolhyj et al. | 562/534 |
| 4,165,300 | 8/1979 | Dolhyj et al. | 252/462 |
| 4,250,346 | 2/1981 | Young et al. | 585/658 |
| 4,256,915 | 3/1981 | Shaw et al. | 562/535 |
| 4,301,038 | 11/1981 | Shaw et al. | 252/468 |
| 4,339,355 | 7/1982 | Deeker et al. | 252/464 |
| 4,358,608 | 11/1982 | Shaw et al. | 562/534 |
| 4,410,450 | 10/1983 | Sasaki et al. | 502/22 |
| 4,520,223 | 5/1985 | McGinnis et al. | 585/629 |
| 4,524,236 | 6/1985 | McCain | 585/658 |
| 4,568,790 | 2/1986 | McCain | 585/658 |
| 4,596,787 | 7/1986 | Manyik et al. | 502/312 |
| 4,892,856 | 1/1990 | Kawajki et al. | 582/267 |

PROCESS AND CATALYST FOR THE PRODUCTION OF ETHYLENE AND ACETIC ACID

This is a continuation of application Ser. No. 07/540,262, filed Jun. 19, 1990, now abandoned.

The present invention relates to a process and catalyst for the production of ethylene and acetic acid.

The catalytic dehydrogenation of ethane is described in a number of patent publications, representative of which may be mentioned for example U.S. Pat. Nos. 4,250,346; 4,524,236 and 4,568,790 and European Patent Publication No. 0294845.

U.S. Pat. No. 4,250,346 discloses the oxidative dehydrogenation of ethane to ethylene in a gas phase reaction at relatively high levels of conversion, selectivity and productivity at a temperature less than 500° C. using as catalyst a composition comprising the elements molybdenum, X and Y in the ratio $$Mo_a X_b Y_c$$

wherein
X is Cr, Mn, Nb, Ta, Ti, V and/or W, and preferably Mn, Nb, V and/or W
Y is Bi, Ce, Co, Cu, Fe, K, Mg, Ni, P, Pb, Sb, Si, Sn, Tl and/or U, and preferably Sb, Ce and/or U,
a is 1,
b is 0.05 to 1.0, and
c is 0 to 2, and preferably 0.05 to 1.0, with the proviso that the total value of c for Co, Ni and/or Fe is less than 0.5.

U.S. Pat. No. 4,524,236 discloses the use of a calcined catalyst of the formula $Mo_a V_b Nb_c Sb_d X_e$ for the oxydehydrogenation of ethane to produce ethylene.

U.S. Pat. No. 4,568,790 discloses a process for the low temperature catalytic oxydehydrogenation of ethane to ethylene in a gas phase using as catalyst a calcined composition of $Mo_a V_b Nb_c Sb_d$ wherein:
a=0.5 to 0.9
b=0.1 to 0.4
c=0.001 to 0.2
d=0.001 to 0.1.

The aforesaid patent publications, although acknowledging the co-production of acetic acid, are primarily concerned with ethylene formation. Recently however in EP-A-0294845 attention has been given to the production of acetic acid.

EP-A-0294845 discloses a process for the selective production of acetic acid by reacting ethane, ethylene or mixtures of ethane and ethylene with oxygen over a catalyst mixture containing (A) a calcined ethane oxidation catalyst containing molybdenum and vanadium and which may optionally contain at least one other metal atom as represented by the general formula $Mo_x V_y Z_z$ in which the metal elements are in combination with oxygen in the form of various oxides and (B) an ethylene hydration catalyst and/or an ethylene oxidation catalyst. In the general formula Z can be nothing or one or more of Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co, Ni and x is equal to 0.5 to 0.9, y is equal to 0.1 to 0.4 and z is equal to 0 to 1.

None of the aforesaid patent publications mention the use of rhenium as a catalyst component, though from U.S. Pat. No. 4,148,757 rhenium is mentioned as one of a multitude of possible components in possibly similar catalysts for the oxidation and/or ammoxidation of olefins.

It has now been found that molybdenum in the aforesaid oxidative dehydrogenation catalysts can be replaced either wholly or partially by either rhenium alone or a combination of rhenium and tungsten and that the product composition depends on the extent and nature of the molybdenum substitution, for example the total substitution of molybdenum by rhenium can substantially eliminate the formation of acetic acid, whereas the partial substitution of molybdenum by rhenium can increase the selectivity to acetic acid.

Accordingly the present invention provides a process for the production from gaseous ethane and/or ethylene of a product comprising ethylene and/or acetic acid, by contacting the ethane and/or ethylene and a molecular oxygen-containing gas at elevated temperature with a calcined molybdenum-containing ethane oxidative dehydrogenation catalyst composition characterized in that molybdenum in the oxidative dehydrogenation catalyst composition is replaced in whole or in part by either rhenium or a combination of rhenium and tungsten.

Also according to the present invention there is provided a molybdenum-containing ethane oxidative dehydrogenation catalyst composition characterized in that molybdenum is replaced in whole or in part by either rhenium or a combination of rhenium and tungsten.

Suitably the catalyst composition comprises the elements A, X and Y in combination with oxygen, the gram-atom ratios of the elements A:X:Y being a:b:c, wherein
$A = Mo_d Re_e W_f$,
X=Cr, Mn, Nb, Ta, Ti, V and/or W, and preferably Mn, Nb, V and/or W,
Y=Bi, Ce, Co, Cu, Fe, K, Mg, Ni, P, Pb, Sb, Si, Sn, Tl and/or U, and preferably Sb, Ce and/or U,
a=1,
b=0 to 2, preferably 0.05 to 1.0,
c=0 to 2, preferably 0.001 to 1.0, and more preferably 0.05 to 1.0 with the proviso that the total value of c for Co, Ni, and/or Fe is less than 0.5,
d+e+f=a,
d is either zero or greater than zero,
e is greater than zero, and
f is either zero or greater than zero.

Preferred catalyst compositions comprise the elements A, Nb, Sb and Z in combination with oxygen, the gram-atom ratios of the elements A:Nb:Sb:Z being a:b:c:g, wherein
A is the same as hereinbefore defined,
Z is at least one of Ca, Ru and Ga, preferably Ca,
a, b and c are the same as hereinbefore defined, and
g is 0 to 2, preferably greater than zero.

More preferred catalyst compositions comprise the elements A, V, Nb, Sb and Z in combination with oxygen, the gram-atom ratios of the elements A:V:Nb:Sb:Z being a:h:b:c:g wherein
A and Z are the same as hereinbefore defined,
a,b,c and g are the same as hereinbefore defined, and
h is 0 to 1.0.

Examples of catalysts suitable for use in the process of the invention include:

$$Mo_{0.56}Re_{0.06}V_{0.26}Nb_{0.07}Sb_{0.03}Ca_{0.02} \quad (III)$$

$$Mo_{0.37}Re_{0.25}V_{0.26}Nb_{0.07}Sb_{0.03}Ca_{0.02} \quad (IV)$$

$W_{0.37}Re_{0.25}V_{0.26}Nb_{0.07}Sb_{0.03}Ca_{0.02}$ (V)

$Mo_{0.24}Re_{0.37}V_{0.26}Nb_{0.07}Sb_{0.04}Ca_{0.02}$, and (VI)

$Re_{0.61}V_{0.26}Nb_{0.07}Ca_{0.02}Sb_{0.04}$ (VII)

It will be understood that the elements are present in combination with oxygen.

As mentioned hereinabove, catalysts (III) to (VI) containing Mo in combination with Re, produce acetic acid from ethane at selectivities which are generally greater than those reported for prior art oxidative dehydrogenation catalysts. On the other hand catalyst (VII) containing Re in the total absence of Mo can produce, from ethane, ethylene substantially free from acetic acid.

The catalyst compositions may be prepared by any of the methods conventionally employed for the preparation of catalysts. Suitably the catalyst may be prepared from a solution of soluble compounds and/or complexes and/or compounds of each of the metals. The solution is preferably an aqueous system having a pH in the range from 1 to 12, preferably from 2 to 8, at a temperature of from 20° to 100° C.

Generally, a mixture of compounds containing the elements is prepared by dissolving sufficient quantities of soluble compounds and dispersing any insoluble compounds so as to provide a desired gram-atom ratio of the elements in the catalyst composition. The catalyst composition may then be prepared by removing the solvent from the mixture. The catalyst may be calcined by heating to a temperature of from 200° to 550° C., suitably in air or oxygen, for a period of from 1 minute to 24 hours. Preferably, the air or oxygen is slowly flowing.

The catalyst may be used unsupported or supported. Suitable supports include silica, alumina, zirconia, titania, silicon carbide and mixtures of two or more thereof.

Further details of a suitable method for preparing a catalyst composition may be found in, for example, EP-A-0166438.

The catalyst may be used in the form of a fixed or a fluidised bed.

The feed gas comprises ethane and/or ethylene, preferably ethane. Ethane produces ethylene and optionally acetic acid. Ethylene produces acetic acid.

Ethane and/or ethylene may be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkenes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane and/or ethylene and the molecular oxygen-containing gas, water (steam) because this can improve the selectivity to acetic acid.

The elevated temperature may suitably be in the range from 200° to 500° C., preferably from 200° to 400° C.

The pressure may suitably be atmospheric or superatmospheric, for example in the range from 1 to 50 bar, preferably from 1 to 30 bar.

Operating conditions and other information applicable to the performance of the invention may be found in the aforesaid prior art, for example U.S. Pat. No. 4,250,346.

The process of the invention will now be further illustrated by reference to the following Examples. In the Examples the following terms are used:

GHSV = Gas Hourly Space Velocity = Volume of gas flowing through catalyst bed (ml/hr)/Volume of catalyst bed (ml).

Ethane conversion (%) =

$$100 \times \frac{[CO]/2 + [CO_2]/2 + [C_2H_4] + [CH_3COOH]/}{[CO]/2 + [CO_2]/2 + [C_2H_4] + [C_2H_6] + [CH_3COOH]}$$

Ethylene selectivity (%) =

$$100 \times \frac{[C_2H_4]}{[CO]/2 + [CO_2]/2 + [C_2H_4] + [CH_3COOH]}$$

Acetic acid selectivity (%) =

$$100 \times \frac{[CH_3COOH]}{[CO]/2 + [CO_2]/2 + [C_2H_4] + [CH_3COOH]}$$

wherein
[ ] = concentrations in mol %
and $[C_2H_6]$ = concentration of unconverted ethane.

CATALYST PREPARATION

In the examples the catalyst compositions are expressed in terms of relative gram-atoms of elements. It will be understood that the elements are present in combination with oxygen.

CATALYST (III)

A catalyst was prepared with the following composition:

$Mo_{.56}Re_{.06}V_{.26}Nb_{.07}Sb_{.03}Ca_{.02}$

Ammonium metavanadate (7.4 g) was added to 80 ml of water and heated at 70° C. with stirring for 15 minutes. To a mixture of niobium pentachloride (4.7 g), antimony trichloride (1.6 g), calcium nitrate (1.0 g) and ammonium perrhenate (4.0 g) was added 40 ml of water. Oxalic acid (7.5 g) dissolved in 40 ml of water was then added and the resulting solution heated at 70° C. with stirring for ca. 15 minutes. The first solution was combined with the second solution and the combined solution heated at 70° C. for 15 minutes. Ammonium molybdate (23.8 g) was dissolved in 80 ml of water with stirring and heated at 70° C. for 15 minutes. This third solution was then added to the combined first and second solutions and the final mixture heated at 70° C. for 15 minutes. The resulting mixture was evaporated to dryness in a large evaporating basin over a hot water bath together with the use of a hot air gun to remove the water as quickly as possible. The solid was dried for 16 hours at 110° C. and then sieved to afford catalyst particles of the correct dimensions. The dried catalyst was calcined at 360° C. for 3.5 hours under a flow of air.

CATALYST (IV)

A catalyst was prepared with the following composition:

$Mo_{.37}Re_{.25}V_{.26}Nb_{.07}Sb_{.03}Ca_{.02}$

Ammonium metavanadate (7.4 g) was added to 80 ml of water and heated at 70° C. with stirring for 15 minutes. To a mixture of niobium pentachloride (4.7 g), antimony trichloride (1.6 g), calcium nitrate (1.0 g) and ammonium perrhenate (16.0 g) was added 40 ml of water. Oxalic acid (7.5 g) dissolved in 40 ml of water was then added and the resulting solution heated at 70° C. with stirring for ca. 15 minutes. The first solution was combined with the second solution and the combined solution heated at 70° C. for 15 minutes. Ammonium molybdate (15.9 g) was dissolved in 80 ml of water with stirring and heated at 70° C. for 15 minutes. This third solution was then added slowly to the combined first and second solutions and the final mixture heated at 70° C. for 15 minutes. The resulting mixture was evaporated to dryness and the solid broken up and calcined as outlined previously.

CATALYST (V)

A catalyst was prepared with the following composition:

$W_{.37}Re_{.25}V_{.26}Nb_{.07}Sb_{.03}Ca_{.02}$

Ammonium metavanadate (7.4 g) was added to 80 ml of water and heated at 70° C. with stirring for 15 minutes. To a mixture of niobium pentachloride (4.7 g), antimony trichloride (1.6 g) calcium nitrate (1.0 g) and ammonium perrhenate (16.0 g) was added 40 ml of water. Oxalic acid (7.5 g) dissolved in 40 ml of water was then added and the resulting solution heated at 70° C. with stirring for ca. 15 minutes. The first solution was combined with the second solution and the combined solution heated at 70° C. for 15 minutes. Ammonium tungstate (23.5 g) was suspended in 60 ml of water and 52 ml of hydrogen peroxide added with stirring. This solution was then heated at 70° C. for 15 minutes. This third solution was then added to the combined first and second solutions and the final mixture heated at 70° C. for 15 minutes. The resulting mixture was evaporated to dryness and the solid broken up and calcined as outlined previously.

CATALYST (VI)

A catalyst was prepared with the following composition:

$Mo_{.24}Re_{.37}V_{.26}Nb_{.07}Sb_{.04}Ca_{.02}$

Ammonium matavanadate (1.7 g) was added to 25 ml of water and heated at 70° C. with stirring for 15 minutes. To a mixture of niobium pentachloride (1.05 g), antimony trichloride (0.5 g), calcium nitrate (0.3 g) and ammonium perrhenate (5.5 g) was added 15 ml of water. Oxalic acid (1.7 g) dissolved in 15 ml of water was then added and the resulting solution heated at 70° C. with stirring for ca. 15 minutes. The first solution was combined with the second solution and the combined solution heated at 70° C. for 15 minutes. Ammonium molybdate (2.4 g) was dissolved in 25 ml of water with stirring and heated at 70° C. for 15 minutes. This third solution was then added to the combined first and second solutions and the final mixture heated at 70° C. for 15 minutes. The resulting mixture was evaporated to dryness and the solid broken up and calcined as outlined previously.

CATALYST (VII)

A catalyst was prepared with the following composition:

$Re_{.61}V_{.26}Nb_{.07}Ca_{.02}Sb_{.04}$

Ammonium metavanadate (2.5 g) was added to 40 ml of water and heated at 70° C. with stirring for 15 minutes. To a mixture of niobium pentachloride (1.55 g), antimony trichloride (0.7 g) and calcium nitrate (0.4 g) was added 20 ml of water. Oxalic acid (3.7 g) dissolved in 20 ml of water was then added and the resulting solution heated at 70° C. with stirring for ca. 15 minutes. The first solution was combined with the second solution and the combined solution heated at 70° C. for 15 minutes. Ammonium perrhenate (13.4 g) was dissolved in 100 ml of water with stirring and heated at 70° C. for 15 minutes. This third solution was then added to the combined first and second solutions and the final mixture heated at 70° C. for 15 minutes. The resulting mixture was evaporated to dryness and the solid broken up and calcined as outlined previously.

CATALYST (VIII)

A catalyst was prepared with the following composition:

$Mo_{.37}Re_{.25}V_{.26}Nb_{.07}Sb_{.03}Ca_{.02}$

A first solution was prepared by dissolving ammonium perrhenate (10.0 g) and ammonium molybdate (9.7 g) in 50 ml of water. A second solution was prepared by adding ammonium metavanadate (4.5 g) to 50 ml of water. A third solution was prepared by adding niobium oxalate (10.2 g), antimony oxalate (1.34 g) and calcium nitrate (0.58 g) to 50 g of water. The solutions were each heated separately, at 70° C. with stirring for 15 minutes. Then the third solution was added to the second solution. The combined solution was heated at 70° C. with stirring for 15 minutes before being added to the first solution and then the resulting mixture was heated at 70° C. with stirring for 15 minutes. The water was evaporated on a hot plate to produce a thick paste before drying at 120° C. in an oven overnight. The resulting solid was ground and screened to 10/30 mesh followed by calcination at 300° C. for 5 hours in static air and screening to 0.5 to 1.0 mm diameter.

CATALYST IX

A catalyst was prepared with the following composition:

$Mo_{0.52}Re_{0.1}V_{.26}Nb_{.07}Sb_{.03}Ca_{.02}$ by the same method as was used for the preparation of Catalyst (VIII), but with the required adjustment in the relative amounts of ammonium perrhenate and ammonium molybdate used.

CATALYST TESTING

CATALYST TESTING METHOD 3 ml of catalyst was loaded into a corrosion resistant stainless steel tube of internal diameter 5.6 mm, and the reactor tube assembly placed in a tubular furnace. The catalyst was then heated to 250° C. at 5° C./min under a flow of air. The desired ethane:air:nitrogen feed gas ratio was then set up in a gas mixing manifold and allowed to pass initially through a preheater zone held at 200° C. and then over the catalyst. The pressure was then adjusted to the required value using a back pressure regulator. Water was added when required into the preheater zone where vaporisation and mixing with the feed gas occurred prior to meeting the catalyst. The product vapours and gases leaving the reactor were sampled and analysed by gas-liquid chromatography (GLC). The temperature was measured by means of a thermocouple inserted into the catalyst bed.

GLC SPECIFICATION:
 Gas Analysis: 3 m Carbosieve S2 Column & Molecular Sieve Column.
 Liquid Analysis: 2.5 m CarboPack B/Peg 20M Column REACTION CONDITIONS
 Reactor Pressure: 14 barg
 GHSV: approx. 3500 $hr^{-1}$
 Feed Composition (by volume): 21% Ethane, 3.8% Oxygen, 75.2% Nitrogen
 Reactor Temperature: In the range 250°–380° C.
 Water Addition Rate: ca 4:1 (Total Gas Feed: Water mole Ratio)
 Catalyst Particle Size: 0.5–1.0 mm diameter.

The normal procedure in screening a catalyst was to set up the feed ratio and flow rates and then increase the temperature in steps, monitoring conversions and selectivities as the experiment progressed. The oxygen concentration slowly decreased with increasing temperature (increasing ethane conversion/combustion) and, as total oxygen deletion approached, water was then cofed to examine the effect on selectivity etc. The results are shown in Table 1.

TABLE 1

| Example | Catalyst | Bed Temp. °C. | Ethane Conversion % | Ethylene Selectivity % | Acetic Acid Selectivity % | Acetic Acid Select. (with water co-feed) % |
| --- | --- | --- | --- | --- | --- | --- |
| 1 | (III) | 325 | 15 | 70 | 21 | — |
| 2 | (IV) | 328 | 12 | 57 | 19 | 43 |
| 3 | (V) | 334 | 11 | 53 | 21 | 49 |
| 4 | (VI) | 332 | 6 | 53 | 28 | 37 |
| 5 | (VII) | 325 | 2 | 61 | 0 | 0 |

Catalyst Testing at Higher Pressure

The catalyst testing method was repeated at 28 barg using Catalyst (VIII) with catalyst particle size of 0.5–1.00 mm dia with 0.27 g/liter gas water co-feed and a feed gas composition of 70% (v/v) ethane, 6.3% v/v oxygen and balance helium. The results are shown in Table 2 in which the contact time is calculated from the ratio of catalyst bed volume to gas flow rate, corrected for temperature and pressure.

TABLE 2

CATALYST (VIII)

| Bed Temperature °C. | Contact time (Seconds) | Ethane Conversion % | Acetic Acid Selectivity % | Ethylene Selectivity % |
| --- | --- | --- | --- | --- |
| 270 | 22 | 5.6 | 72.6 | 16.7 |
| 270 | 27 | 7.3 | 70.5 | 18.4 |
| 270 | 35 | 7.7 | 65.7 | 20.4 |
| 270 | 55 | 13.3 | 77.5 | 12.3 |
| 277 | 55 | 14.3 | 78.0 | 12.1 |
| 288 | 35 | 10.9 | 69.5 | 17.9 |
| 303 | 25 | 9.1 | 60.4 | 26.7 |
| 326 | 20 | 9.9 | 53.3 | 35.0 |
| 300 | 25 | 8.9 | 62.8 | 25.0 |
| 300 | 40 | 12.5 | 70.2 | 16.7 |

Catalysts (VIII) and (IX) with catalyst particle sizes of 0.5–1.0 mm diameter were also tested at 28 barg with 0.27 g water per liter of gas in feed and a feed gas composition of 70% (v/v) ethane, 6.3% (v/v) oxygen and balance helium. The results are shown in Table 3 which shows the effect on selectivity of varying the amount of rhenium in the catalyst.

TABLE 3

| Catalyst | Contact Time | Bed Temperature °C. | Ethane Conversion % | Acetic Acid Selectivity % | Ethylene Selectivity % |
| --- | --- | --- | --- | --- | --- |
| (VIII) | 22 | 267 | 5.3 | 73.1 | 16.1 |
| (IX) | 22 | 267 | 4.98 | 48.0 | 39.8 |
| (VIII) | 20.7 | 303 | 8.17 | 61.1 | 27.2 |
| (IX) | 20.7 | 303 | 10.81 | 51.5 | 34.7 |
| (VIII) | 20.0 | 325 | 9.955 | 53.0 | 34.8 |
| (IX) | 20.0 | 325 | 9.05 | 46.1 | 42.2 |

I claim:

1. A process for the production from gaseous ethane and/or ethylene of a product comprising ethylene and/or acetic acid, said process comprising the step of contacting the ethane and/or ethylene and a molecular oxygen-containing gas at elevated temperature with a catalyst composition comprising the elements A, X and Y in combination with oxygen, the gram-atom ratios of the elements A:X:Y being a:b:c, wherein $A = Mo_d Re_e W_f$, X represents at least one element selected from the group consisting of Cr, Mn, Nb, Ta, Ti, V and W,
Y represents at least one element selected from the group consisting of Ce, Sb and U,
a = 1
b = 0.05 to 1.0,
c = 0.001 to 1.0,
d + e + f = a,
d is zero or greater than zero,
e is greater than zero, and
f is zero or greater than zero.

2. A process as claimed in claim 1 in which ethylene and optionally acetic acid are produced from gaseous ethane.

3. A process as claimed in claim 1 in which X represents at least one element selected from the group consisting of Mn, Nb, V and W.

4. A process as claimed in claim 1 in which the catalyst composition comprises the elements A, Nb, Sb and Z in combination with oxygen, the gram-atom ratios of the elements A:Nb:Sb:Z being a:b:c:g wherein A, a, b, and c are as defined in claim 1,
Z represents at least one element selected from the group consisting of Ca, Ru and Ga, and
g is 0 to 2.

5. A process as claimed in claim 1 in which the catalyst composition comprises the elements A, V, Nb, Sb and Z in combination with oxygen, the gram-atom ratios of the elements A:V:Nb:Sb:Z being a:h:b:c:g wherein A, a, b and c are as defined in claim 1, Z represents at least one element selected from the group consisting of Ca, Ru and Ga, g is 0 to 2, and h is 0 to 1.0.

6. A process as claimed in claim 1 in which the catalyst composition is selected from the group consisting of:

$Mo_{0.56} Re_{0.06} V_{0.26} Nb_{0.07} Sb_{0.03} Ca_{0.02}$,
$Mo_{0.37} Re_{0.25} V_{0.26} Nb_{0.07} Sb_{0.03} Ca_{0.02}$,
$W_{0.37} Re_{0.25} V_{0.26} Nb_{0.07} Sb_{0.03} Ca_{0.02}$,
$Mo_{0.24} Re_{0.37} V_{0.26} Nb_{0.07} Sb_{0.04} Ca_{0.02}$,
$Re_{0.61} V_{0.26} Nb_{0.07} Ca_{0.02} Sb_{0.04}$, and
$Mo_{0.52} Re_{0.1} V_{0.26} Nb_{0.07} Sb_{0.03} Ca_{0.02}$, the elements being present in combination with oxygen.

7. A process as claimed in claim 1 in which the ethane and molecular oxygen-containing gas are contacted with the catalyst composition in the presence of steam.

* * * * *